United States Patent [19]

Kendall et al.

[11] Patent Number: 5,730,711
[45] Date of Patent: Mar. 24, 1998

[54] WRIST/HAND SUPPORT DEVICE

[76] Inventors: David Kendall, 1492 S. 900 West, Salt Lake City, Utah 84104; Sheldon L. Black, Sr., P.O. Box 1699, Colorado City, Ariz. 86021; Floyd E. Black, P.O. Box 205, Colorado City, Ariz. 86021

[21] Appl. No.: 609,675

[22] Filed: Mar. 1, 1996

[51] Int. Cl.[6] ............... A61F 5/00; B43L 15/00
[52] U.S. Cl. ............... 602/64; 602/21; 248/118
[58] Field of Search ............... 602/5, 20, 21, 602/64; 128/112.1, 113.1, 117.1, 118.1; 248/118, 118.1, 118.5

[56] References Cited

U.S. PATENT DOCUMENTS

| 8,065 | 4/1851 | Goshon et al. |
|---|---|---|
| 89,142 | 4/1869 | Gorsline . |
| 310,257 | 1/1885 | Cowan . |
| 520,711 | 5/1894 | Shea . |
| 793,756 | 7/1905 | Williams . |
| 1,510,877 | 10/1924 | Weidenmann . |
| 1,627,635 | 5/1927 | Craig . |
| 5,265,835 | 11/1993 | Nash . |
| 5,355,888 | 10/1994 | Thomsen . |
| 5,439,192 | 8/1995 | King . |
| 5,445,349 | 8/1995 | Hart ............... 248/118 |

*Primary Examiner*—Richard J. Apley
*Assistant Examiner*—Denise Pothier
*Attorney, Agent, or Firm*—Thorpe North & Western, L.L.P.

[57] ABSTRACT

A wrist support device including a compressible support or pillow configured for positioning under the hand and wrist of a user, a stabilizing adapter plate and a glide plate disposed below the compressible support/pillow which enables the support/pillow to glide over a planar support surface smoothly and quietly. The compressible pillow is especially configured to receive the wrist in order to hold the wrist in a natural position without interfering with the ability of the user to type or perform other skills using a keyboard.

20 Claims, 5 Drawing Sheets

WRIST/HAND SUPPORT DEVICE

BACKGROUND OF THE INVENTION

1. Field of the Invention

The present invention relates to a wrist support device and, in particular, to a device which is used to support the base of a user's hand and the bones of the wrist when performing repetitive motions, such as typing or data entry on a computer keyboard, thereby preventing the development of repetitive stress disorders, such as carpal tunnel syndrome.

2. Prior Art

Due to the widespread use of computers and other word processing equipment, the number of persons using keyboards to enter data and perform other tasks which involve repetitive movements of the fingers and hands has greatly increased. With these increases in the number of users has also come an increased understanding of the risks which repetitive stresses raise regarding the health of those using such devices. The most common are repetitive stress disorders such as carpal tunnel syndrome—a disorder which can lead to debilitating pain in the wrists of those who use typewriters, keyboards and other data entry devices.

Carpal tunnel syndrome is believed to develop as the hands and wrists of the user are held in an unnatural position during repetitive tasks performed over a prolonged period of time which place stress on the wrist. The most common scenario is that of a secretary or data entry person who spends long hours entering information into a computer via the computer's keyboard.

Figure 1A:
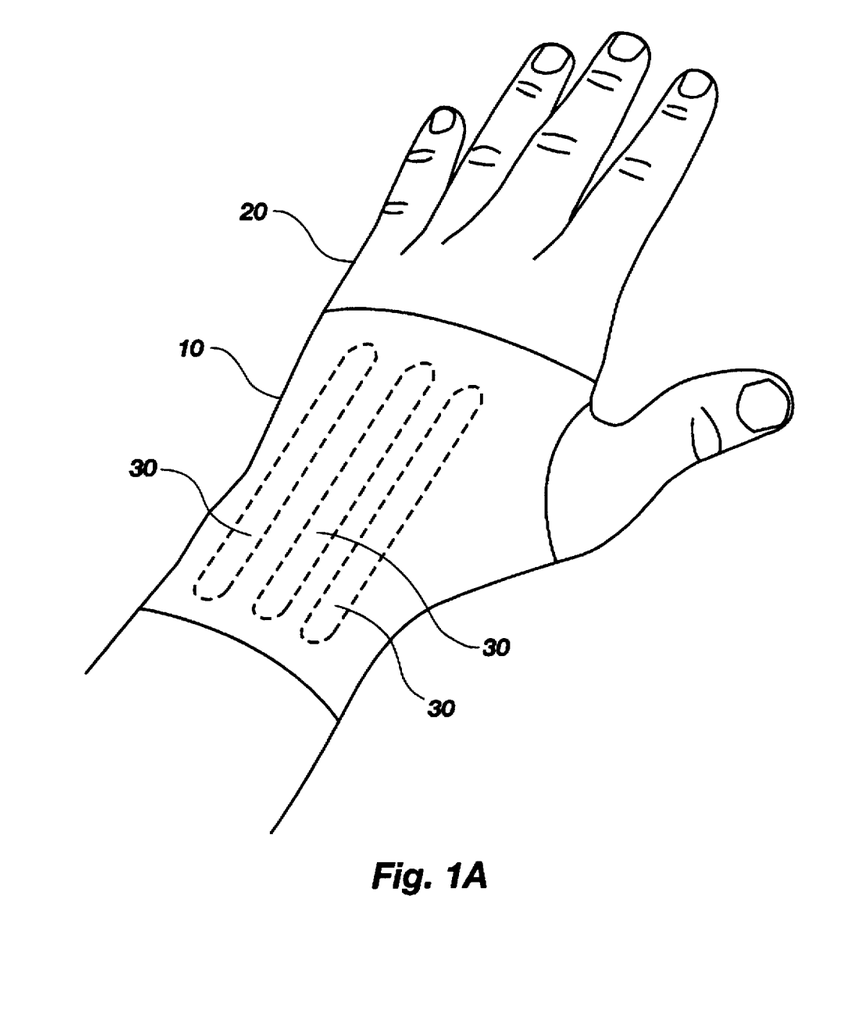
FIG. 1A shows a perspective view of a wrist support brace for preventing repetitive stress disorders made in accordance with the teachings of the prior art.

To avoid the pain suffered by employees and the loss of valuable employee time which accompany repetitive stress disorders, several devices have been created to reduce the risk of persons getting carpal tunnel syndrome. One common device, shown in FIG. 1A, is a wrist support brace, generally indicated at 10, which is worn about the wrist and lower part of the user's hand, generally indicated at 20. The wrist support brace 10 has braces 30 formed therein to prevent the wrist from bending and causing stress on the damaged or inflamed carpal tunnel within the wrist. However, such devices are generally not favored because they are inconvenient, time consuming and awkward to put on and to remove by oneself. Additionally, the braces restrict all movement of the wrist, may put pressure on the inflamed or damaged wrist, and are generally unsightly. Thus, the wrist support braces 10 are generally only worn by those who are already suffering from wrist pain due to repetitive stress disorders.

Figure 1B:
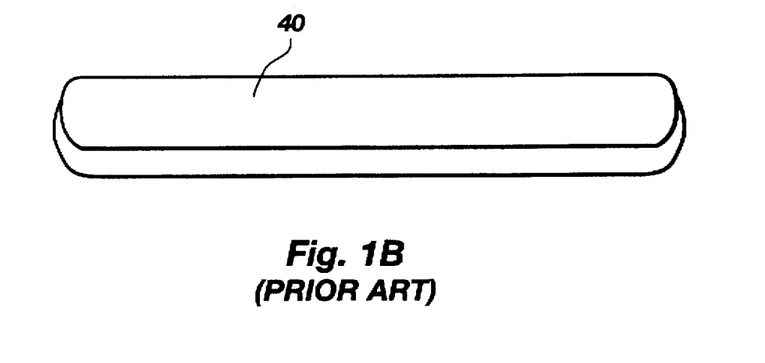
FIG. 1B shows a perspective view of a wrist support pad made in accordance with the teachings of the prior art.

Another device which has gained significant popularity is an elongate pad 40, shown in FIG. 1B. The elongate pad 40 is typically made of neoprene or some other somewhat pliable material and is positioned in front of the keyboard so that the user's hands or wrists may rest on the pad while typing. Unfortunately, the pad does not move with the user's hands or wrists. As a user moves his or her hands, the material of the elongate pad tends to irritate the skin on the bottom of the wrist as the two rub against one another. Those who work for prolonged hours using such a device often suffer pronounced irritation on the underside of the hand and wrist. The irritation can lead to chaffing, which in turn leads to the loss of bodily fluids, such as sweat and blood, thereby raising an unsanitary condition. Furthermore, many such pads are made of materials which are not convenient to clean whether due to porousness of the material, or cloth coverings which cannot be conveniently removed.

An additional concern with the elongate pads 10 is that they can actually cause stress on the wrist. If the bony portion of the user's wrist (i.e. the portion including the pisiform) is placed above the pad, the lack of support under the other wrist bones, especially those near the base of the thumb, causes the user's hand/wrist to rotate into a generally horizontal position. The natural position for a persons hand/wrist is an incline of between 10 and 30 degrees. As the wrist and the user's hand are held in a horizontal position, the elbow is forced to rotate outwardly and additional stress is placed on the wrist, as gravity continually pulls down on the elbow.

To overcome these concerns, many users place the elongate pad directly below the soft tissue between the bones of the wrist and the radius and ulna, minimizing the amount of rotation. However, in such a position, the weight of the arms and hands places pressure on the soft tissues and on the tendons of the wrist. This, in turn, raises concerns of repetitive stress disorders.

While other suggestions have been made regarding the attachment of wrist supports to a user's arm, see e.g. U.S. Pat. No. 1,510,877, such devices are generally not desirable because they move with the user's hands when lifted away from the keyboard. Thus, for example, if the hands of a person periodically leave the keyboard to pick up or move materials, the support devices go with the user's hands, potentially interfering with the other task. Additionally, having a support device strapped to one's wrist is generally unattractive and will bother many people with sensitive skin. Furthermore, if the strap is securely placed around the wrist, additional pressure would be applied to the carpel tunnel and actually increase the risk of repetitive stress disorders, rather than helping reduce the risk of the same.

Thus, there is a need for a device which supports the wrists of a user while not placing pressure on the wrist area when working on a keyboard, or similar device which causes repetitive stress, and which will move planarly with the wrist of the user. Such a device should also be configured to remain on the planar support surface along which it travels when the user's hands are pulled away from the keyboard to perform other tasks.

SUMMARY OF THE INVENTION

Thus, it is an object of the present invention to provide a wrist support device which supports the hand and bony portion of the user's wrist when typing or performing other similar repetitious movements of the fingers and hands to thereby relieve pressure on the user's wrist.

It is another object of the present invention to provide such a device which is movable with the user's wrists, both to the sides and forward and backward relative to the keyboard being used.

It is yet another object of the present invention to provide such a device which need not be attached to the user's hands, wrists or arms, so that the device may remain in place when the user's hands are drawn away from the keyboard, etc.

It is still another object of the present invention to provide such a device which will easily move along a planar support surface, such as a desk, without marring or marking the planar support surface.

It is an additional object of the present invention to provide such a device which is easy to use and inexpensive to manufacture.

Another object of the present invention is to support the user's hands in a natural position so as to minimize stress on the user's wrists, and which provides a soft cushion to decrease tender areas on the wrist and hands causes by pressure from the weight of the arms.

Yet another object of the present invention is to provide such a device to receive portion of the wrist under the pisiform (heal of the wrist), thereby forcing the user to properly position the device under the bones of the wrist rather than the soft tissue of the wrist.

A further object of the present invention is to provide such a device in which the portion of the wrist support which is commonly contacted by the user's hand and wrist may be readily sanitized with common cleaning chemicals.

Still yet another object of the present invention is to make such a support which can be conveniently used on high friction materials such as neoprene "mouse" pads.

The above and other objects of the invention are realized in specific illustrated embodiments of a wrist support device including a compressible support or pillow configured for positioning below the hand and wrist of a user, and a glide plate disposed below the compressible support/pillow which enables the support/pillow to glide over a planar support surface smoothly and quietly.

In accordance with one aspect of the invention, the compressible pillow has an outer covering which is formed of a flexible material which conforms to the shape of the projection formed by the bones of the user's wrist (commonly referred to as the heel of the hand), and in particular the pisiform, when the user's hand/wrist is placed thereon. The compressible pillow provides padding to the bones of the hand and wrist, and supports the hand and wrist in a position which relieves pressure on the soft tissue of the user's wrist. The compressible pillow also allows prolonged use without irritating the skin of the wrist or causing sore spots thereon.

In accordance with another aspect of the present invention, the flexible material frictionally engages the skin overlying the pisiform and extends below the lower hand and the soft tissue of the wrist. As the hand and wrist are moved laterally and toward and away from the keyboard, the wrist support device moves with the user's hand and prevents the position of the hand from causing unnecessary pressure on the wrist. This prevents the damage caused by lack of support, but gives the user full range of movement. Additionally, because the wrist support devices move with the user's hands and wrists, they do not irritate the skin after prolonged use, as is common with the embodiment of FIG. 1B. Furthermore, because of the frictional engagement between the wrist supports and the user's wrists, the devices need not be attached to the user's wrists, as do many movable devices of the prior art. Thus, the user need not repeatedly attach and detach the wrist supports when periodically moving between use of the keyboard and other matters.

In accordance with an additional aspect of the present invention, the compressible pillow has an upper side which is configured to conform to the bones which form the heel of the hand, and in particular the pisiform. The compressible pillow supports the wrist while preventing sore spots on the wrist, and holding the hand in a more natural position. Rather than forcing the hand to remain generally horizontal during typing, the configuration of the compressible pillow allows the fingers to strike the keys with little, if any, rotation and encourages the hand to remain in its natural position after the key stroke has been completed.

In accordance with another aspect of the invention, the glide mechanism is in the form of a piece of soft material which may be repeatedly moved over a working surface, such as a desk, without marring the surface. In a preferred embodiment, the glide mechanism is formed of a piece of felt. Unlike balls or other materials of the prior art, the felt can be moved thousands of times across a work surface without marking or marring the surface.

In accordance with yet another aspect of the present invention, the glide plate includes a piece of hard plastic which will glide across neoprene and other rubber-like materials with little friction. The material enables a person to use the device on pads used for a mouse or other pointer controlling devices which are designed to be high in friction.

In accordance with another aspect of the present invention, the material forming the compressible pillow is formed of polypropylene or other similar material which can be easily sanitized with conventional cleaning materials. If the wrist supports are used by several different people, the surface on which the user's wrist will rest can be conveniently sanitized after each use to prevent the transmission of unhealthy bacteria. If the wrist support is used by a single person, the wrist supports can be cleaned periodically, i.e. weekly, to prevent the build-up of body odors caused by perspiration.

By continued use of such a wrist support, it has been found that a significant decrease in fatigue and injury can be achieved for those who spend prolonged periods of time working on typewriters and computer keyboards. The user's wrists are fully supported without the skin irritation and other problems of the prior art. Additionally, the small size of the wrist supports make them more convenient for movement between computers for those who routinely work on keyboards at different locations.

BRIEF DESCRIPTION OF THE DRAWINGS

The above and other objects, features and advantages of the invention will become apparent from a consideration of the following detailed description presented in connection with the accompanying drawings in which.

DETAILED DESCRIPTION

Reference will now be made to the drawings in which the various elements of the present invention will be given numeral designations and in which the invention will be discussed so as to enable one skilled in the art to make and use the invention. It is to be understood that the following description is only exemplary of the principles of the present invention, and should not be viewed as narrowing the pending claims.

Figure 2:
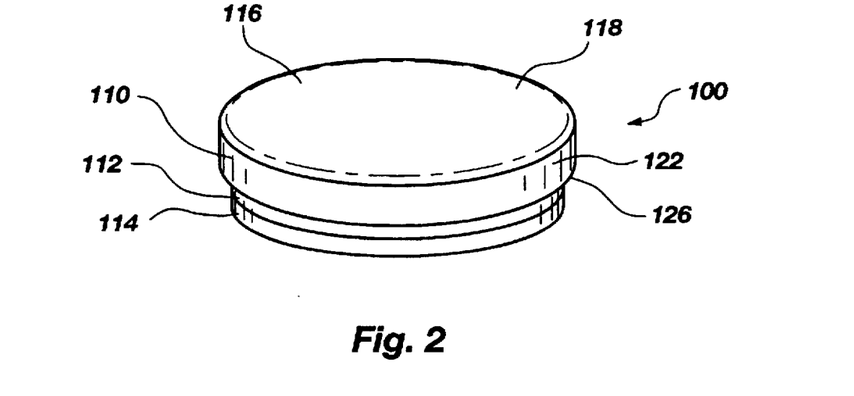
FIG. 2 shows a perspective view of a hand support device made in accordance with the principles of the present invention.

Referring to FIG. 2, there is shown a perspective view of one embodiment of a hand support device, generally indicated at 100, made in accordance with the principles of the present invention. The hand support device 100 includes a compressible support or pillow 110 which is attached to a stabilizing adapter plate 112. The stabilizing adapter plate 112 is typically made of a hard plastic, and is attached to a glide plate 114. The compressible pillow 110 is typically formed of a resilient shell 116 having an upper surface 118, an annular biasing sidewall 122 which extends downwardly from the upper surface, and a lower surface 126 to which the stabilizing adapter plate 112 is attached. The adapter plate 112, in turn, has a bottom surface to which the glide plate 114 is attached.

The upper surface 118 is generally nonconvex, i.e. planar or somewhat concave, and is typically formed by a resilient, plastic material, such as polypropylene, which has a high coefficient of friction with human skin. When a wrist or hand is placed on the upper surface 118, the upper surface will generally model or form slightly to conform to the curvatures of the wrist or hand. Because the maximum compressibility of the pillow 110 typically occurs in the middle, a hand/wrist position which most people find comfortable to use with the device 110 is to place the skin overlying the pisiform in the center of the upper surface 118. As will be explained in additional detail below, such a positioning of the pisiform holds the hand in a comfortable, natural position which places less stress on the soft tissue of the wrist than previous wrist supports. This position results in a reduction in tension within the soft tissue of the wrist and a decrease in fatigue by those using the device 100.

An additional advantage of forming the shell 116 out of polypropylene or a vinyl material is that the shell, and in particular the upper surface 118, can be easily cleaned with conventional cleaning materials. By cleaning the shell 116 often, the transmission of diseases, both those of the skin and those commonly transferred by the hands, can be avoided. Additionally, odors which can develop due to bacterial growth can be eliminated.

In contrast to the present invention, the pads 40 (FIG. 1B) of the prior art are generally made of materials which cannot be easily sanitized or deodorized. Thus, many people have their own pad, thereby increasing the cost to the business or user.

For ease of manufacture, the sidewall 122 and the lower surface 126 are also typically formed of a material similar to that used for the upper surface 118. Numerous different vinyls and similar materials can be used to provide an appropriate blend of flexibility and frictional interaction with human skin.

The glide plate 114 is attached to the stabilizing adapter plate 112 which is attached to the lower surface 126 of the compressible pillow 110. The glide plate 114 is typically made of a piece of material, preferably felt, which is slightly smaller in diameter than the diameter of the compressible pillow 110. The outer diameter of the felt should be at least a majority of the diameter of the compressible pillow to prevent rotation of the wrist causing the compressible pillow to contact a planar support surface along which the device 100 is being slid. If the outside diameter of the felt glide plate 114 is too small, the high friction material of the shell 116 will catch on the surface and prevent continued sliding. Those skilled in the art will appreciate that the glide plate need not be one continuous piece. For example, four smaller pieces of felt could be placed adjacent the sidewall at the perimeter of the lower surface 126 of the shell 116. Such placement would provide an "effective outer diameter", i.e. the extreme outer edges of the piece(s) of felt would be disposed for the felt pieces to prevent the shell 116 from catching on the planar support surface along which the device is moved.

Figure 2A:
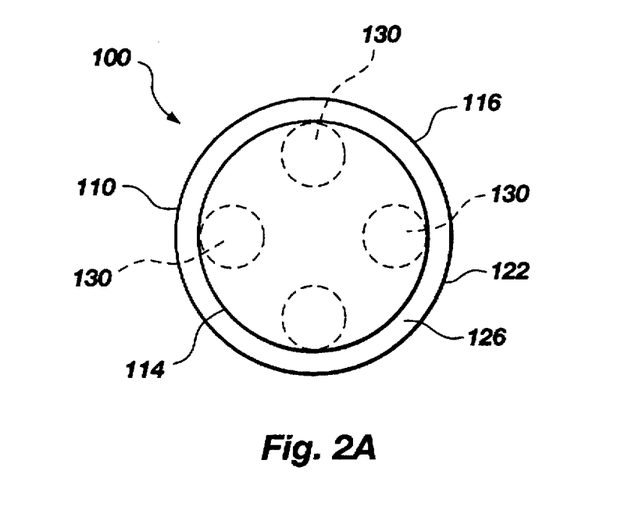
FIG. 2A shows a bottom view of the hand support device of FIG. 2.

FIG. 2A shows a bottom view of the wrist support device 100 of the present invention. The glide plate 114 is formed of a circular piece of felt so that it covers substantially all the stabilizing plate which is attached to the lower surface 126 of the compressible pillow 110. As was explained earlier, the felt glide plate 114 could be replaced by a plurality of smaller pieces 130 disposed about the perimeter of the stabilizing plate 112 (FIG. 1) to keep the compressible pillow 110 from contacting the surface along which the glide plate moves.

Figure 3:
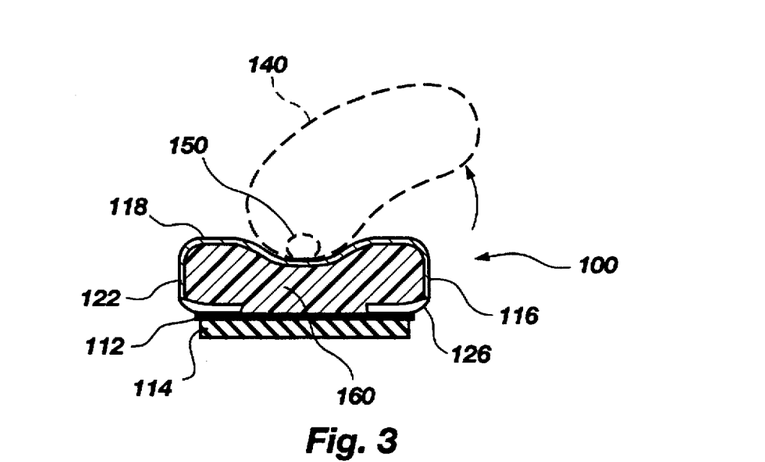
FIG. 3 shows a cross-sectional view of the hand support device shown in FIG. 2, and a human hand positioned on the hand support device.

Referring now to FIG. 3, there is shown a cross-sectional view of the wrist support device 100, and a dashed figure representing the normal position the wrist 140 at the base of a human hand (as opposed to the soft tissue between the wrist bones and the radius and ulna). When a human hand is placed on a horizontal planar support surface, it is usually most comfortable for the wrist to be positioned at an incline of between about 10 and 30 degrees as shown. If the hand is placed flat on the planar support surface, the elbow must either be rotated outwardly or the pressure within the wrist will cause fatigue within a short period of time.

Those who routinely use a computer keyboard for prolonged periods of time generally find that efforts to keep their elbows rotated outwardly sufficiently to relieve stress in the wrist results in fatigue in the arms and upper back. The present invention solves these concerns by encouraging or biasing the wrist 140 to stay in its natural position. As the wrist 140 is placed on the upper surface 118 of the compressible pillow, the small bone which extends downwardly from the wrist, i.e. the pisiform 150, nests into the compressible pillow at approximately the center of the upper surface. Thus, rather than turning the wrist 140 into an unnatural position, the compressible pillow 110 helps bias to and maintain the wrist comfortably.

The projection of the skin adjacent the pisiform 150 into the upper surface 118 of the compressible pillow 110, causes the wrist support device 100 to move with the hand and wrist 140 of the user. Thus, for example, if the user must enter numbers from a 10-key pad at the far end of the computer keyboard, the user's right hand may be slid down to the 10-key pad without moving the left hand and without lifting the right hand/wrist off the support device 100. With the elongate pad 40 of the prior art, repeated movements without lifting the hand/wrist would cause irritation to skin as the skin rubbed along the bar with each move.

By providing two supports, the present invention also allows the user to move both hands independently. Thus, to reach a key at the back of the key board, the left hand may be moved forward with the wrist support device 100, while the right hand is being moved rearwardly on another wrist support device, or vice-versa. By allowing independent movement without the need to lift each hand from the support, the present invention significantly decreases the overall strain on the user's arms and hands.

Also shown in FIG. 3 is a cushioning material or filler 160, such as a polymer foam, which may be disposed within the shell 116 to add resiliency to the shell and additional support to the wrist. The filler 160 is held in place by the shell 116 on the top and sides and by the stabilizing adapter plate 112 on the bottom. If desired, the stabilizing adapter plate 112 or the glide plate 114 can be removable to allow replacement if for some reason the glide plate or filler becomes unusable, or the respective pieces can be attached to one another to prevent disassembly.

The filler 160 could also be used as a novelty, for example the shell 116 could be made of a clear material and the filler 160 a colored gel. In the alternative, a filler 160 with a picture formed therein could also be used.

Figure 4:
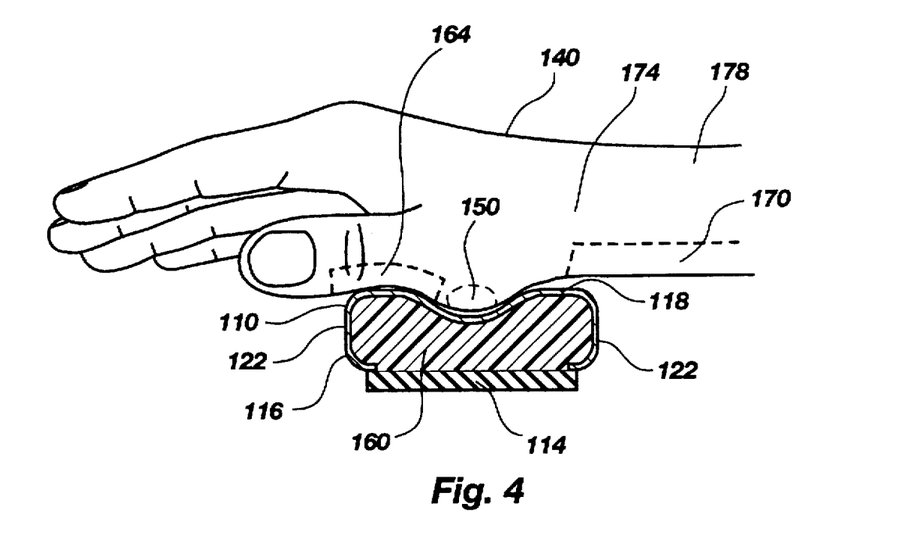
FIG. 4 shows a cross-sectional view of the hand support device and a fragmented view of a human hand, wrist and lower arm.

Referring now to FIG. 4, there is shown a cross-sectional view of the wrist support device 100, and a fragmented view of a human hand, wrist and arm. For reasons which will be discussed below, the stabilizing adapter plate 112 (FIGS. 2 and 3) has been omitted. Because the embodiment shown in FIGS. 2 through 3 is substantially round, the cross-sectional view provided in FIG. 4 appears substantially the same as that in FIG. 3. While it is believed that most wrist support devices 100 made in accordance with the present invention will be round due to cost and ease of manufacture, numerous other shapes may be used.

When the compressible pillow 110 of the support device 100 is positioned under the bones of the wrist 140 so that the projection caused by the pisiform 150 contacts an approximate center of the upper surface 118, the outer edge of the compressible pillow 110, as represented by the sidewall 122, extends forward to a position beneath the outermost metacarpal bone 164 (which is attached to the small finger). The compressible pillow 110 also extends rearwardly to a position adjacent the end of the ulna 170. However, because of the projection formed by the pisiform 150, the outer edge of the compressible pillow 110 supports these areas rather than placing a significant amount of pressure on them. If the hand or arm must be rotated forwardly or rearwardly, the compressible pillow 110 allows the movement and helps encourage the hand or arm back to the original position. Thus, the user's hand is always encouraged or biased into a position which causes the least amount of stress.

By spreading support throughout the bones of the wrist 140, the metacarpal bone 164 and the ulna 170, very little pressure is placed on the soft tissue 174 between the bones of the wrist 140 and the lower arm 178. Thus, the device 100 significantly decreases fatigue in the user and greatly decreases the risk of repetitive stress disorders such as carpal tunnel syndrome. It also prevents the projection formed by the pisiform 150 from developing sore areas due to prolonged forceful contact with hard surfaces such as desks.

The stabilizing adaptor plate 112 (FIGS. 2 and 3) is omitted from FIG. 4 to show that it is not essential to the present invention. The stabilizing adapter plate 112 adds support to provide a firmer feeling to the compressible pillow 110, and also facilitates attachment of the glide plate 114 to the compressible pillow. However, the stabilizing adapter plate 112 can be omitted for those who like a soft feeling to the cushion. The glide plate 114 attaches directly to the lower surface 126 of the compressible pillow 110 with adhesive, and holds the filler 160 inside.

Figure 5:
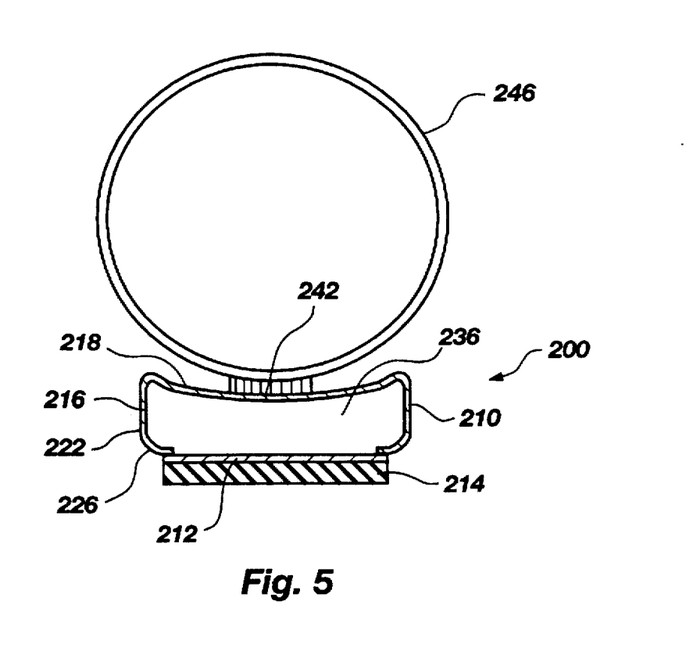
FIG. 5 shows a cross-sectional view of an alternate embodiment of the present invention.

Referring now to FIG. 5, there is shown a cross-sectional view of another embodiment of the present invention. The wrist support device 200 includes a compressible pillow 210, a stabilizing adapter plate 212 and a glide plate 214. The compressible pillow 210 includes a shell 216 having an upper surface 218 which is concave, an annular sidewall 222, and a lower surface 226. The shell 216 is disposed to form a void 236 which is filled with air. When the stabilizing adapter plate 212 is adhesively attached to the lower surface 226, the air within the void provides support for the compressible pillow 210. If desired, a small needle may be inserted in the shell 216 when it is sufficiently hot to inject air into the void 236. The hot plastic will then seal itself as the needle is withdrawn. Those skilled in the art will recognize several materials which will perform as described.

As shown in FIG. 5, the upper surface 218 of the shell 216 has a concave portion. The curvature assists the user in finding the proper position for the wrist by feel, rather than requiring the user to look at the wrist support device 200 each time the user's hands are removed. Thus, a user may repeatedly remove his or her hands from the devices to perform other tasks, and then properly position the devices when typing is recommenced. To properly facilitate placement of the area about the pisiform in the concave portion, the concave portion should be less than 2 inches, and preferably about 1 inch.

Also shown in FIG. 5 is a hook and loop fastener 242 which can be used to hold a wrist band 246 to the support device 200. The wrist band 246 may be provided for those who wish for the support devices 200 to be held to the wrist at all times. However, because of the concave upper surface 218 into which the wrist can nest, and because of the low friction glide plate 214, the device will move easily with the user's hand. The only occasion which it is anticipated that the wrist band 246 will be desirable is where the user must constantly move between keyboards, etc., on different work surfaces. Thus, for example, a secretary having a computer keyboard on a desk, a typewriter on a credenza and a 10-key adding machine on a small side-stand may wish to have the support devices 200 move with his or her hands from work surface to work surface.

Figure 6:
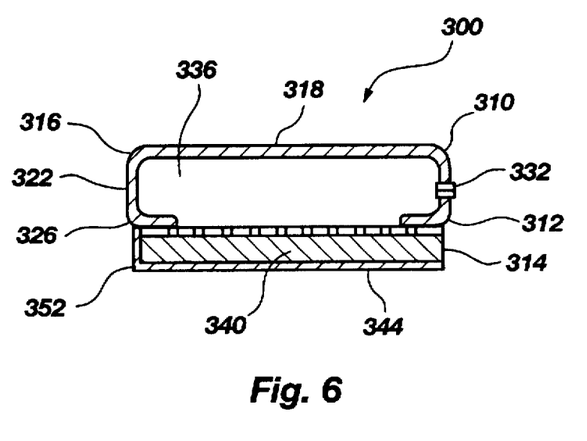
FIG. 6 shows a cross-sectional view of yet another embodiment of the present invention.

Referring now to FIG. 6, there is shown yet another embodiment of the present invention. The wrist support device, generally indicated at 300, includes a compressible pillow 310 attached to a stabilizing adapter plate 312 and a glide plate 314. The compressible pillow 310 includes a shell 316 having an upper surface 318, an annular sidewall 322, and a lower surface 326. A valve 332 is provided in the sidewall 322 to allow the user to change the amount of air held within the void 336. Thus, the amount of cushioning provided by the compressible pillow can be adjusted to the preferences of the user.

The glide plate 314 includes a piece of material 340, such as felt, as in the prior embodiments. However, a thin layer of a hard, low friction plastic layer 344, such as EVA, is provided. The plastic layer 344 allows the wrist support device 300 to slide on high friction materials, such as neoprene. Those familiar with computers will recognize that neoprene and similar materials are commonly used for "mouse" pads. Thus, the hard plastic layer 344 allows the support device 300 to slide.

Typically the plastic layer 344 will be adhesively attached to the material 340 of the glide plate 314. However, those skilled in the art will appreciate that the material of the glide plate 314 could be omitted. If such were done, however, the thickness or effective diameter of the plastic layer 344 would need to be increased so that the high friction material forming the shell 316 would not routinely come into contact with the high friction neoprene.

Additionally, the plastic layer 344 could be provided separately from the material 340 of the glide plate 314. When the wrist support device 300 is to be used on a neoprene pad or other high friction material, the plastic layer 344 could be attached to the material 340 with adhesive layer or some other removable attachment device, such as a clamp 352.

Thus there is disclosed an improved wrist support device. Those skilled in the art will appreciate that numerous modifications can be made without departing from the scope and spirit of the invention. The appended claims are intended to cover such modifications.

What is claimed is:

1. A wrist support device for preventing repetitive stress disorders in a wrist of the user as the wrist and bones contained therein moves above a planar support surface, the device comprising:

wrist support means for supporting the user's wrist, the wrist support means being made of a compressible material and having upper and lower surfaces disposable below the wrist of the user, the upper surface defining a concave portion therein at least when engaged by a projection in the user's wrist formed by a pisiform bone in the wrist, the upper surface being configured to frictionally engage the projection of the user's wrist formed by the pisiform during planar movement above the planar support surface;

biasing means circumscribing the concave portion and interposed between the upper surface and the lower surface for biasing the wrist to a laterally inclined orientation and nesting the wrist into the approximate center of the upper surface; and a gliding means adjacent to the lower surface of the wrist support means for facilitating movement of the wrist support means along the planar support surface.

2. The wrist support device of claim 1, wherein an outer edge of the upper surface is elevated with respect to the upper surface to bias the wrist to the inclined orientation.

3. The device of claim 2, wherein the inclined orientation is within the range of 10 to 30 degrees.

4. The device of claim 1, wherein the wrist support means comprises a compressible support including an outer shell formed of a resilient material defining an inner portion filled with a compressible material.

5. The wrist support device of claim 4, wherein the shell of the compressible support means is formed of a polypropylene vinyl.

6. The device of claim 4, wherein the inner portion is filled with air.

7. The device of claim 6, further comprising means for adjusting the amount of air contained in the inner portion.

8. The device of claim 4, wherein the inner portion is filled with a compressible foam.

9. The device of claim 1, wherein the gliding means comprising a generally planar material disposed so as to cover a majority of the lower surface, the gliding means being disposed such that planar movement of the user's wrist causes the gliding means to slide along the planar support surface.

10. The device of claim 9, wherein the gliding means comprises at least one piece of fabric.

11. The device of claim 10, wherein the at least one piece of fabric comprises felt.

12. The device of claim 1, wherein the gliding means comprises plastic.

13. The device of claim 1, further comprising support means for holding the upper surface to the user's wrist.

14. The device of claim 13, wherein the support means comprises a removable band for wrapping about the user's wrist, and attachment means for securing the band to the wrist support means.

15. The device of claim 1, wherein the wrist support means is round and wherein gliding means is round.

16. The device of claim 15, wherein the upper surface has a diameter of less than 2 inches.

17. The device of claim 1, wherein the wrist support means has an outer diameter, and wherein the gliding means has an effective outer diameter which is slightly smaller than the outer diameter of the wrist support means.

18. The device of claim 1, further comprising a stabilizing adapter plate disposed between the wrist support means and the gliding means.

19. The device of claim 18, wherein the stabilizing adapter plate is made of plastic.

20. The device of claim 18, wherein the stabilizing adapter plate is adhesively attached to the wrist support means and wherein the gliding means is adhesively attached to the stabilizing adapter plate.

* * * * *